United States Patent [19]

Aguadisch et al.

[11] Patent Number: 5,480,653
[45] Date of Patent: Jan. 2, 1996

[54] FORMULATIONS FOR SUSTAINED RELEASE DRESSINGS AND THEIR USE

[75] Inventors: Louis M. J. Aguadisch, Valbonne; Alain Etienne, Grasse, both of France

[73] Assignee: Dow Corning France S.A., Valbonne, France

[21] Appl. No.: 890,334

[22] Filed: May 26, 1992

Related U.S. Application Data

[63] Continuation of Ser. No. 598,295, Oct. 16, 1990, abandoned.

[30] Foreign Application Priority Data

Oct. 23, 1989 [FR] France ................... 89 13819

[51] Int. Cl.$^6$ ................ A61K 9/10; A61K 9/70; A61K 47/34; A61L 15/26
[52] U.S. Cl. ............... 424/486; 424/443; 424/445; 424/425; 514/947
[58] Field of Search ............ 424/425, 443–445, 424/447–449, 485–488; 523/122; 514/947, 772.3

[56] References Cited

U.S. PATENT DOCUMENTS

| | | | |
|---|---|---|---|
| 3,996,934 | 12/1976 | Zaffaroni | 424/449 |
| 4,053,580 | 10/1977 | Chien et al. | 424/425 |
| 4,189,546 | 2/1980 | Deichert et al. | 528/26 |
| 4,230,686 | 10/1980 | Schopflon et al. | 424/425 |
| 4,814,184 | 3/1989 | Aguadisch et al. | 424/78 |

*Primary Examiner*—Edward J. Webman
*Attorney, Agent, or Firm*—Robert L. McKellar

[57] ABSTRACT

The invention concerns a sustained release formulation comprising an agent (A) which is to be released and a vehicle (B) therefor.

The vehicle comprises a hydrophilic component such as a polyhydroxylated organic substance such as a polyethylene glycol, glycerol, sorbitol, mannitol or lactose and curable silicone composition which is capable of curing at ambient temperature and contains a polysiloxane having alkylhydrogen units, a polysiloxane having unsaturated groups and a platinum or rhodium catalyst. The formulation may be applied to the human or animal body or a cavity in the latter to cure in situ to give a dressing capable of sustained release of the therapeutic or diagnostic agent (A) to the body.

The invention is applicable in the field of pharmacy.

12 Claims, No Drawings

FORMULATIONS FOR SUSTAINED RELEASE DRESSINGS AND THEIR USE

This is a continuation of application Ser. No. 07/598,295 filed on Oct. 16, 1990 abandoned.

This invention is concerned with formulations for sustained release dressings and their use.

Numerous proposals have been made for sustained release products, especially for example, in the field of delivery of therapeutic and/or diagnostic materials to the human or animal body. Prior proposals include, for example, external application of a transdermal patch to the body, insertion of a preformed implant into the body, attachment of a dressing to the tissue of a cavity and oral administration of a preformed element containing an active substance intended for administration orally.

In the field of controlled release of therapeutic and diagnostic agents into the human or animal body from implants, it is known to employ silicone based materials as a matrix or membrane through which a lipophilic agent is able to diffuse at a controlled rate into the body. Silicone based materials proposed for the purpose are generally inert to body fluids and therefore highly acceptable for use in the body. However, the rates at which therapeutic and other compounds are released from or through silicone materials are generally very low due to the diffusion characteristics from the silicone matrix and are generally considered to be "first order" i.e. the quantity of substance liberated is a linear function of the square root of time. This is beneficial for controlled release of those therapeutic and other agents which are required to be introduced to the body at a comparatively low rate over a long period of time. However, it would be beneficial if a wide range of therapeutic and other agents could be delivered into the body at a comparatively high rate of more than several mg to one g per day for one or more days or even weeks, at an at least substantially constant rate independent of time, which is to say at zero order release rate. For these requirements the silicone based materials employed heretofore have been regarded as unsuitable due to the need to employ lipophilic agents whose rate of diffusion through the silicone material is slow. In the field of dressings which may be applied for example to the exterior of the body or to a natural cavity thereof it is desirable to employ a material which is capable of remaining in the chosen location for a period of time during which a therapeutic or diagnostic agent may be delivered at a desired rate. One of the requirements is thus a prolonged residence time coupled, in some cases, with an ability to release the agent at a constant rate over a period of several hours or days.

We have now found that one may provide an element formed in situ on or in the human or animal body, hereinafter referred to as a dressing, capable of releasing a therapeutic or diagnostic agent at a desired rate during several hours to several days or more by use of a formulation comprising a room temperature curable silicone composition, a hydrophilic component and a therapeutic or diagnostic agent (A).

The present invention provides in one of its aspects a sustained release formulation suitable for use as a dressing in or on the human or animal body comprising an agent (A), and a vehicle (B) therefor which comprises a hydrophilic component (a) and a curable silicone composition (b) which is formulated to cure at room temperature within 10 minutes of mixing and application to a human or animal body comprising a polysiloxane having alkylhydrogen siloxane units, a polysiloxane having unsaturated groups for reaction therewith and a platinum or rhodium catalyst for the hydrosilylation reaction.

The invention is concerned with formulations for forming dressings for the human or animal body which are capable of delivering a therapeutic or diagnostic agent to the body. It is a characteristic of the invention that the dressings are formed in situ by use of a formulation which comprises a silicone composition which is curable in a short time after mixing and application to the body. The dressing may be formed by coating a formulation according to the invention onto intact or damaged skin or by casting the formulation into a natural or artificial cavity of the body. The cavity may be for example the occular, buccal, nasal, aural, vaginal or rectal cavity or a cavity developed for example in a tooth or an open wound. The formulation is allowed to cure in situ. Characteristics of the dressings may be controlled within wide limits by appropriate selection of the components.

The agent (A) of a formulation according to the invention is a material capable of release from a dressing formed by use of the formulation when the dressing is exposed to biological fluids of the human or animal body, i.e. when the dressing is in an aqueous environment. Suitable materials include those agents (A) which are not soluble in or do not diffuse through silicone materials i.e. those materials which are hydrophilic and include therapeutic or diagnostic agents. The agent (A) may be a solid or liquid material and is incorporated into the formulation before curing of the formulation. It is important to ensure that the agent (A) chosen does not interfere with the curing of the silicone composition to an unacceptable extent. The invention is especially applicable to those therapeutic and diagnostic agents which it is desired to deliver to the body over a period of time at a controlled rate. As is known the rate of delivery required of a given drug falls within a therapeutic window. By tailoring a formulation according to the invention it is possible to provide dressings from which many drugs can be delivered at rates within their therapeutic window. Therapeutic or diagnostic agents suitable for use as the agent (A) of the present invention include those which are intended to be released into the body via the blood stream and may be hydrophilic or lipophilic substances. The agent (A) may be chosen in accordance with normal pharmaceutical practice and will normally have a pH appropriate to the conditions at the region in the body where it is to be released. Normally, the pH anticipated is greater than 4.5. If the pH is more acidic, then a suitable buffer substance may be used to modify the properties of the dressing to permit a more suitable swelling and/or release profile. Therapeutic agents which may be employed include for example antibiotic, antiseptic, antiinflammatory, cardiovascular, antihydrogen, bronchodilator, analgesic, antiarrythmic, antihistamine, α-1 blocker, beta blocker, ACE inhibitor, diuretic, antiaggregant, sedative, tranquiliser, anticonvulsant and anticoagulant agents, vitamins, agents for treating gastric and duodenal ulcers, proteolytic enzymes, healing factors, cell growth nutrients and peptides. Specific examples of suitable therapeutic agents include penicillins, cephalosporins, tetracyclines, macrolides, epinephrine, amphetamines, aspirin, barbiturates, catecholamines, benzodiazepine, thiopental, codeine, morphine, procaine, lidocaine, sulphonamides, tioconazole, perbuterol, furosamide, prazosin, prostaglandins, salbutamol, indomethicane, diclofenac, glafenine, dipyridamole and theophylline. Some of the operative therapeutic and diagnostic agents may contribute to the activities of the hydrophilic component and may modulate the rate of delivery of the agent (A). This factor influences the proportion of agent (A) present in the formulation, as does the extent to which the agent (A) may inhibit or accelerate the cure of the formulation. The proportion of the agent (A)

employed in a formulation according to the invention is chosen in accordance with the concentration of the agent (A) required in the dressing to deliver the dosage required at the proposed delivery rate and may be varied within a very wide range. The agent (A) may provide a major or a minor amount of the formulation. The efficient delivery achieved with dressings made from formulations according to the invention permits use of comparatively low dosage levels. However, it is generally desirable to include as large a proportion of therapeutic or diagnostic agent as possible consistent with the desired delivery of the agent.

The silicone polymer formed by curing the silicone composition of the formulation serves as a binder matrix for the other components and ingredients, and may be employed to generate a greater or lesser proportion of the matrix depending on the intended site of application and the use for which the dressing is intended. For example, those formulations which are intended for the formation of dressings by casting into a body cavity preferably employ from 40 to 80% more preferably up to 60% of the silicone composition by weight of the vehicle, to ensure sufficient shape retention during use or to restrict the rate of release of the agent (A). If desired the formulation may comprise additional ingredients, for example fillers (which may be, for example opaque to X rays or other diagnostic radiation), extenders, for example silicone fluids, and excipients employed in pharmacy and compounds intended to perform as pH buffers in controlling the environment immediately in and around the dressing when it is in an aqueous environment.

Release of the agent (A) from a dressing prepared from a formulation according to the invention is dependent upon presence of water in the environment in which the dressing is present. No swelling occurs, and at least substantially no release of the agent (A) takes place until the dressing is in contact with an aqueous medium. When the dressing is exposed in an aqueous environment the dressing swells, at least to a small extent, as a result of intake of water and then the agent (A) is progressively released. The rate at which the agent (A) is released appears to be dependent upon the surface area of the dressing and the extent to which the dressing swells, and this extent is dependent upon the quantity and pH of the aqueous environment of the dressing and upon the dissolution rate and/or the contribution to hydrophilic or modulating activity of the agent (A), upon the nature of the hydrophilic component (a) and upon the nature of other components of the formulation. The mechanism by which this phenomenon occurs is not fully understood. However, without wishing to be bound by any particular theory, we believe that in one aspect the silicone polymer (which has a measure of elasticity) and the hydrophilic component in combination are essential for satisfactory sustained release through a combination of elastomeric and osmotic properties, the hydrophilic component serving to draw water into the dressing, for example to provide a hypertonic environment and to cause the silicone polymer to become distended, and also to co-operate with attempted contraction of the distended silicone polymer to deliver the agent (A) to the surrounding medium from the dressing.

In a formulation according to the invention, the hydrophilic component (a) is preferably a liquid at relevant temperatures, but solid materials (for example sorbitol, manitol, sodium chloride and certain drugs) dissolved in suitable solvent may be used. This component is suitably an organic hydrophilic material having two, more preferably three or more, hydroxyl groups per molecule and may be chosen, for example, from the liquid polyethylene glycols having a molecular weight in the range of 100 to 600, propylene glycol, glycerol, sorbitol and mannitol. The hydrophilic component is preferably a hygroscopic material. Whilst some swelling and release of the agent (A) takes place from dressings having each of these as the hydrophilic component, we prefer to use a material which is a liquid at the temperature at which the agent is to be released, and preferably also liquid at the temperature at which the dressing is made. The hydrophilic component selected preferably does not interfere unduly with curing of the formulation. This component is most preferably selected from the water soluble, polyhydric alcohols having a melting point of less than 25° C. The most preferred material is glycerol. In order to ensure release of the agent (A) at a desired rate from the dressing, we prefer to employ the hydrophilic component in the formulation in a proportion within the range of 5 to 40% by weight of the vehicle. If less than 5% by weight of the hydrophilic component is present the beneficial effects are not realised, whereas if more than 40% is employed not only are the beneficial effects not realised, but also the cure characteristics of the curable silicone may be very adversely influenced and/or some or all of the hydrophilic material may be lost from the dressing. Proportions within the range specified may be selected with regard to the intended life cycle time of the dressings. In general, when glycerol is used, we prefer to employ from 10% to 25% glycerol by weight of the vehicle.

A formulation according to the invention preferably also comprises a modulating component which controls delivery of the agent (A) from the dressing formed upon curing of the formulation. If no modulating component is present in the dressing, a burst of the agent (A) is delivered from the dressing initially at a somewhat high rate followed by a somewhat reduced rate until the dressing is no longer capable of delivering the agent (A). The modulating component serves to modulate the release of the agent (A) and may be selected in accordance with the modulation desired. For example, those materials which do not swell substantially in water may be expected to modulate the delivery of the agent (A), to improve the constancy of the delivery of the agent (A) and the proportion released and possibly also lengthen the overall useful life of the dressing. When a faster constant delivery is desired, a modulating component may be employed which swells substantially in water in order to modulate the delivery of the agent (A) to enhance the period during which the agent is delivered at a somewhat higher rate, with a consequently short overall useful life of the dressing.

The modulating component may be selected from a wide range of organic materials. Modulating components which do not swell substantially in biological fluids encountered by dressings include organic hydrophilic substances (I) having two or more hydroxyl groups per molecule. Modulating components which serve to promote release of the agent (A) at a high rate include hydrophilic polymers (II) which swell in an aqueous medium. The particular substance (I) or polymer (II) used, and the proportion employed in the formulation, are selected in accordance with the rate of delivery and the period during which delivery is required and the nature of the dressing required. The substances (I) serve to regulate or eliminate the initial burst of the agent from the dressing and may extend the life of the dressing during which the drug is delivered at a constant and optionally comparatively high rate. In contrast, polymers (II) serve to increase the ability of the dressing to swell and consequently serve to increase the ability of the dressings to discharge the agent at a very high rate even though the aqueous media which are available on the body or in cavities thereof is present in comparatively small volume.

The organic hydrophilic substance (I) may have two, more preferably three or more hydroxyl groups per molecule and may be chosen, for example, from the polyethylene glycols having a molecular weight in excess of 600, sorbitol, mannitol, lactose and mixtures thereof. The material used is selected in accordance with the characteristics required of the dressing and especially the release profile desired in the selected location for the dressing. We prefer to use a material which is a solid at the temperature at which the formulation is prepared and a solid at the temperature at which the agent (A) is to be released. We prefer to employ a material which is hygroscopic. The substance is most preferably selected from the water soluble, polyhydric alcohols having a melting point of greater than about 40° C. The organic substance may also preferably be selected from the group consisting of the solid polyethylene glycols of molecular weight greater than 600, sorbitol, mannitol and lactose and is present to an extent from 5% to 25% by weight of the vehicle. The most preferred substance (I) is sorbitol. In order to ensure release of the agent (A) at a desired rate when dressings formed from the formulation are subjected to biological fluids, we prefer to employ the sorbitol in the formulation in a proportion of up to 40%, more preferably the hydrophilic agent comprises from 5 to 25% by weight of the vehicle.

The hydrophilic polymer (II) may be any one, or a mixture of any two or more, of those organic polymers known to be capable of swelling in aqueous media of pH as found in biological fluids at the intended site of the dressing, i.e. greater than about 4.5 for natural body cavities, provided that it does not interfere unduly with curing of the formulation. Generally, in order to achieve prolonged fast delivery of the agent (A) it is preferred that the polymer exhibit significant swelling as determined by its water inhibition during a short time. The polymer may be chosen, for example from the group consisting of cellulosic materials, e.g. cellulose and cellulose derivatives for example carboxymethylcellulose, sodium carboxymethyl cellulose whether crosslinked or not, hydroxypropylcellulose and acetylated chitin. The potential of these polymers to swell should be borne in mind especially in those cases where the dressing is likely to be subjected to copious wetting. In the absence of copious amounts of water however, the swelling of these polymers is limited.

Some of these polymers (II) swell in aqueous medium of pH >4 and may be caused to swell at more acidic pH, if desired, by incorporation of a salt capable of performing as a buffer to modify the physiological pH at which the dressing swells. We have found that swelling of dressings comprising sodium carboxymethylcellulose may be induced to a desired extent to release agent (A) in aqueous medium of pH 4 or less by inclusion of sodium acetate in the formulation. However, the time required for curing formulations including such salts is extended and their use is generally not preferred in those subject formulations which are intended to cure very rapidly. The hydrophilic polymer (II) which is selected from the group consisting of hydroxypropyl cellulose, carboxymethyl cellulose and sodium carboxy methyl cellulose, whether crosslinked or not, is preferably present to an extent of 10% to 45% by weight of the vehicle.

Certain of the swellable polymers (II) suitable for use in the invention, for example sodium carboxy methylcellulose, contribute not only to swelling and to the ability of the dressing to release the agent (A) but also to bioadhesive characteristics of the dressing, i.e. the ability of the dressing to adhere to the skin or mucosa of the body. Bioadhesive characteristics of the dressing may also be promoted by presence in the vehicle of certain polymers and copolymers of acrylic acid (e.g. polyacrylic acid cross linked with polyalkyl sucrose or 3,4-dihydroxy-1,5-hexadiene), acrylates e.g. poly(hydroxyethyl methacrylate), vinylpyrrolidones, vinyl acetate, polycarboxylic acids, poly(ethylene oxide), alginates, gelatin, pectin, pectin derivatives, natural gums, proteins, pharmaceutically active salts of these and mixtures thereof. The property of greater or lesser adhesion of the swollen dressing to the body is pertinent to the intended mode of use of the dressing. For example, in some cases it may be advantageous to have good adhesive properties to ensure that the dressing adheres well to body tissues, whereas in other cases it may be advantageous if the adhesive properties are poor. The adhesive properties conferred also appear to be dependent on the degree of swelling and therefore pH dependent. For example, dressings which contain sodium carboxymethylcellulose as a modulating component are substantially non-adhesive to body tissues in aqueous medium of pH 1 to 3.5, but adhere well in aqueous media at pH 4 to 8 such as are normally found in biological fluids in the body cavities. In addition to the possibility to design formulations to make dressings having bioadhesion, it will be apparent that dressings which contain a hydrophilic substance (I) as modulating agent and which are not intended to swell substantially, may also contain a swellable polymer (II) to induce bioadhesion. This may be especially beneficial, for example, in dressings intended for application to the buccal, nasal or occular cavities and possibly the rectal or vaginal cavities where the extent of swelling is restricted by the smaller proportions of aqueous medium present.

The curable silicone composition of a formulation according to the invention is curable to a cellular or non-cellular gel or elastomeric form in which it serves to bind, i.e. contain or entrap, the other components of the formulation and may provide a major or minor proportion of the formulation. The composition is curable at room temperatures i.e. 20°±5° C. and thus permits the formulation to be used to provide in situ cured dressings. The polysiloxanes employed have silicon-bonded unsaturated organic groups, e.g. vinyl groups, available for reaction with silicon-bonded hydrogen atoms in presence of a hydrosilylation catalyst for example a platinum or rhodium compound. The addition reaction which occurs is appropriate to yield chain extended or crosslinked unfoamed resinous or elastomeric silicone products.

Suitable polysiloxanes having unsaturated groups for reaction with polysiloxanes having silicon-bonded hydrogen atoms include polydiorganosiloxanes which have sufficient unsaturated groups for formation of the polymer network, for example polysiloxanes having siloxane units according to the general formula

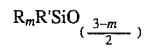

in which each R represents a monovalent hydrocarbon group having up to 20 carbon atoms, for example a lower alkyl or phenyl group e.g. a methyl radical, m is 1 or 2 and R' represents an aliphatically unsaturated group, for example cyclohexenyl or a group R"CH═CHR'", where R" represents a divalent aliphatic chain linked to the silicon atom and R'" represents a hydrogen atom or an alkyl group; examples of groups R' are thus vinyl, allyl and hexenyl. These polysiloxanes also comprise units

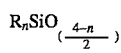

in which R is as referred to above, and n is 1, 2 or 3. Preferably, these polysiloxanes have from 0.01% to 1% by weight of aliphatically unsaturated groups and a viscosity of the order of about 10 mm$^2$/s to about 25000 mm$^2$/s. More preferably their viscosity lies in the range 100 mm$^2$/s to 2000 mm$^2$/s.

Suitable polysiloxanes having alkylhydrogensiloxane units include polymers having units according to the general formula

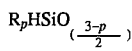

in which each R represents a monovalent hydrocarbon group containing 1 to 20 carbon atoms, for example a lower alkyl or phenyl group e.g. a methyl group and p is 1 or 2. The alkylhydrogen polysiloxanes may also comprise units

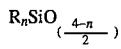

as referred to above. Preferably this polysiloxane has from 0.5% to 2.5% by weight of silicon-bonded hydrogen atoms. We prefer that each R represents a methyl group. Preferably, terminal groups of the alkylhydrogen polysiloxane have the formula $R_3SiO_{1/2}$ where each R represents a methyl group. Suitable alkylhydrogen polysiloxanes include those comprising MeHSiO units with or without the presence of $Me_2SiO$ units and having viscosities of the order of from about 1 to about 1000 mm$^2$/s more preferably from about 5 to about 50 mm$^2$/s.

The formulations cure within 10 minutes or more preferably within five minutes or less of mixing, so that the patient is required to remain immobile for only a short time whilst curing takes place. In order to achieve satisfactory cure it is important that the ratio of silicon-bonded hydrogen atoms of the polysiloxanes to all groups reactive therewith in the formulation is appropriate, so that enough of the alkylhydrogen polysiloxane is present to effect the desired cure. We have found it possible to provide formulations according to the invention which cure within three minutes or less of mixing of the formulation at room temperature and humidity (i.e. about 60% to 80% relative humidity). The curing time is dependent on various factors, including the type and proportion of other components present in the formulation and especially the salt materials, which tend to retard the cure significantly. The rate at which the agent (A) is released from the dressing is also dependent to some extent upon the resilience of the silicone polymer.

Platinum catalysts may take any of the known forms, ranging from platinum as deposited on carriers such as silica gel or powdered charcoal, to platinic chloride, salts of platinum and chloroplatinic acids. A preferred form of platinum is chloroplatinic acid either as the commonly obtainable hexahydrate or the anhydrous form, on account of its easy dispersibility in organosilicon systems and its non-effect on colour of the mixture. Platinum complexes may also be used e.g. those prepared from chloroplatinic acid hexahydrate and divinyl tetramethyldisiloxane. It is desired to prolong the cure time one may include in the composition one of the known platinum catalyst inhibitors such as cyclic polymethylvinylsiloxane compound or an acetylenic alcohol e.g. methyl butynol but these are not generally preferred in a formulation according to the invention. The rate of cure of the formulation from which the vehicle (B) is formed is dependent not only upon the silicone polymer forming ingredients but also upon the nature of the other ingredients of the mixture, including the agent (A) and any salts present during the curing. Presence of ionic salts, e.g. sodium acetate, in the formulation tends to extend the cure time and in such cases it is desirable to reduce or eliminate the proportion of inhibitor present and/or to increase the proportion of platinum catalyst employed.

If desired foaming of the silicone composition as it cures may be induced, for example by inclusion among the silicone forming materials of a polysiloxane having silicon-bonded hydroxyl groups with a view to reaction with the polysiloxane having silicon-bonded hydrogen atoms as more fully described for example in U.S. Pat. No. 4,026,845, and/or by inclusion of water or an aliphatic alcohol (for example a primary aliphatic or araliphatic alcohol for example a lower aliphatic monofunctional alcohol having up to 12 carbon atoms, e.g. ethanol, n-propanol, or benzyl alcohol) or by inclusion in the composition of a volatile blowing agent as more fully described for example in U.S. Pat. No. 4,550,125. Preferred foamable formulations include compounds having silicon-bonded or carbon-bonded hydroxyl groups which foam and cure in presence of a platinum catalyst according to the scheme $\equiv$SiH+HOQ$\rightarrow$ $\equiv$SiOQ+H$_2$. The group Q may be for example an aliphatic group or a polysiloxane having one or more reactive hydroxyl groups so that by virtue of the plurality of silicon-bonded or carbon-bonded hydroxyl groups the hydrogen evolved as a gas serves to form cells within the developing network of interconnected polysiloxane chains. Curable silicone compositions employed for preparation of cellular dressings may also comprise foam stabilisers or surfactants. Suitable materials include fluorinated silicones.

If desired, other adjuvants may be incorporated in the silicone composition for example fillers, colorants, coloured indicators, extenders, diluents and processing aids for example cyclic or linear polydiorganosiloxanes. The presence of some silica filler is desirable when dressings having strongly elastomeric properties are required.

Formulations according to the invention are curable at room temperature when mixed, and therefore are normally used to produce sustained release dressings immediately upon mixing the various components. In those cases in which it is desired to store the formulation prior to admixture and formation of a drug delivery dressing, this may be achieved by storing the formulation in separate parts one of which contains the catalyst for the curable silicone composition and one of which contains the alkylhydrogen polysiloxane. When the agent (A) is present in the formulation during storage, it may be preferable to include it in one only of the parts of the formulation in order to preserve its effectiveness.

A formulation according to the invention preferably comprises from 10 to 70% by weight of the agent (A) and from 90 to 30% by weight of the other components of the formulation in a proportion of 10 to 40 parts by weight of the hydrophilic component, 40 to 80 parts by weight of the polysiloxanes and 10 to 40 parts by weight of a hydrophilic substance (I) selected from the group consisting of polyethylene glycols of molecular weight greater than 600, sorbitol, mannitol and lactose.

The present invention offers numerous advantages. The silicone and other materials chosen enable sustained release dressings to be formed by simple and easily controlled methods in situ which cure into a desired shape and have selected combinations of properties (e.g. bioadhesion, release rate and release profile). One may produce the formulations and process them without imposing severe processing conditions upon incorporation of the substance to be released, e.g. high temperatures or pressures, which might be damaging to medicaments used. The silicone materials and other ingredients used are acceptable in the human or animal body. The dressings may be formulated to give a moderate to rapid release of agent (A), which is in many cases highly advantageous in that high zero order release rates of from 1 to 100 mg per day over several days may be achieved. The drug delivery profile of dressings according to the invention may be predetermined by appropriate selection of the types and proportions of components and ingredients used. A particular advantage of dressings according to the invention is their ability to release agent (A) at a controlled rate in substantially larger proportion than heretofore achieved with silicone materials. We have found for example that both lipophilic and hydrophilic agents may be released from the dressings. It is a further advantage of the present invention that the dressings can be elastomeric materials able to withstand many of the pressures exerted during normal activities of the patient.

In order that the invention may become more clear there now follows a description of various formulations, Example 5 being illustrative of the invention. In the Examples, all parts and percentages are expressed by weight.

The Examples show the dependence of cure rate upon the components of the formulation and show the dependence of swelling of dressings upon the components of the formulation and the dependence of bioadhesion and drug delivery upon swelling.

The silicone materials employed in the Examples were as follows:

Silicone Part 1A comprised 69 parts of dimethyl vinyl endblocked polydimethylsiloxane fluid having a viscosity at 25° C. of about 2,100 mm²/s, 6 parts hexamethyl disilazane, 1 part water, 0.1 part of a platinum catalyst, being a complex of chloroplatinic acid hexahydrate and vinyl siloxanes, and 24 parts of fume silica;

Silicone Part 1B comprised 88 parts of the dimethylvinyl endblocked polysiloxane, 12 parts of a copolymer of polydimethyl and polymethylhydrogen siloxanes having a viscosity at 25° C. of about 5 mm²/s and 0.75% hydrogensiloxane units (as % H) and 0.4 part methylvinyl cyclic polysiloxanes;

Silicone Part 2A comprised silicone Part 1A with an additional 1% of the platinum catalyst;

Silicone Part 2 B comprised silicone Part 1B without the cyclic siloxanes;

Silicone Part 3A comprised silicone Part 1A with an additional 2% of the platinum catalyst;

Silicone Part 4A comprised silicone Part 1A with an additional 0.5% of the platinum catalyst;

Silicone Part 5A comprised silicone Part 1A with an additional 0.3% of the platinum catalyst;

Silicone Part 6A comprised silicone Part 1A with an additional 0.2% of the platinum catalyst;

Silicone Part 7A comprised silicone Part 1A with an additional 0.1% of the platinum catalyst;

Cellulosic materials used in the Examples were as follows:

Cellulosic material 1 was a sodium carboxymethylcellulose supplied under the trade name Tylopur 1000 by Hoechst;

Cellulosic material 2 was a hydroxypropyl methylcellulose phthalate supplied under the trade name HP50 by Seppic having an average molecular weight of 20,000 and a carboxybenzoyl groups content of 20 to 24%;

Cellulosic material 3 was a hydroxypropyl methylcellulose phthalate supplied under the trade name HP55 by Seppic having an average molecular weight of 20,000 and a carboxybenzoyl group content of 27 to 35%;

Cellulosic material 4 was a blend of microcrystalline cellulose and sodium carboxymethylcellulose supplied under the trade name Avicel RC591 by Seppic having an average particle size of 28 micrometers;

Cellulosic material 5 was a crosslinked sodium carboxy methyl cellulose supplied under the trade name ACDI SOL by Seppic having a degree of substitution of 0.6 to 0.85;

Cellulosic material 6 was a hydroxypropyl methylcellulose supplied under the trade name METOLOSE 60S H50 by Seppic having an average molecular weight of about 8,600, and Cellulosic material 7 was a methyl cellulose supplied under the trade name METOLOSE SM15 by Seppic having approximately 30% of methoxy groups.

Solutions referred to as having specified pH were prepared as follows:

pH=1.2 and pH=2 were made from a KCl, HCl buffer (Carlo Erba);

pH=3, 4, 5 and 6 were made from a potassium biphthalate buffer (Carlo Erba);

pH=7 and 8 were made from $KH_2PO_4$ buffer (Carlo Erba);

pH=4.5 was made according to USP XX1 from an acetate buffer.

EXAMPLE 1

In this Example, the effect of varying the proportions of catalyst and inhibitor upon the cure rate of the silicone composition is demonstrated. Formulations were prepared using 8 parts of a mixture of a silicone Part A and silicone Part B using different ratios of Part A to Part B, 2 parts of tetracycline and optionally with a hydrophilic material. The drug was mixed with the Part A, the Part B added and the formulation mixed for 1 minute. The time taken for the formulation to become cured at room temperature, as demonstrated by its transition from a stiff liquid to a solid mass, was noted. The results are shown in Table 1 and Table 1(a).

TABLE 1

| Formulation | Silicone Part A | Silicone Part B | Ratio Part A: Part B |
|---|---|---|---|
| 1 | 1A | 2B | 8:3 |
| 2 | 1A | 2B | 6:5 |
| 3 | 2A | 2B | 10:1 |
| 4 | 2A | 2B | 8:3 |
| 5 | 2A | 2B | 6:5 |
| 6 | 3A | 2B | 10:1 |
| 7 | 3A | 2B | 8:3 |
| 8 | 3A | 2B | 6:5 |
| 9 | 4A | 1B | 8:3 |
| 10 | 4A | 2B | 10:1 |
| 11 | 4A | 2B | 9.5:1.5 |
| 12 | 4A | 2B | 9:2 |
| 13 | 4A | 2B | 8.5:2.5 |
| 15 | 4A | 2B | 8:3 |
| 16 | 4A | 2B | 6:5 |
| 17 | 5A | 2B | 7:4 |
| 18 | 5A | 2B | 8:3 |
| 19 | 5A | 2B | 8:3 |
| 20 | 5A | 2B | 8:3 |
| 21 | 5A | 2B | 8:3 |
| 22 | 5A | 2B | 8:3 |
| 23 | 5A | 2B | 8:3 |
| 24 | 5A | 2B | 8:3 |
| 25 | 5A | 2B | 8:3 |
| 26 | 5A | 2B | 8:3 |
| 27 | 5A | 2B | 8:3 |
| 28 | 6A | 2B | 8:3 |
| 29 | 7A | 2B | 8:3 |

TABLE 1-continued

| Formulation | Silicone Part A | Silicone Part B | Ratio Part A: Part B |
|---|---|---|---|
| 30 | 7A | 2B | 6:5 |

TABLE 1 (a)

| Formulation | Hydrophylic Substance | Cure Time (mins) | Remarks |
|---|---|---|---|
| 1 | — | 40 | V. tacky - poor consistency |
| 2 | — | — | No cure after 2 hours |
| 3 | — | 12 | Tacky |
| 4 | — | 2.5 | No tack - good surface |
| 5 | — | 1 | |
| 6 | — | 10 | Tacky |
| 7 | — | 2.5 | No tack - good surface |
| 8 | — | <1 | |
| 9 | — | 35 | Good surface |
| 10 | — | 13 | Very tacky |
| 11 | — | 8 | Very tacky |
| 12 | — | 5 | Tacky |
| 13 | — | 3.5 | Slight tack |
| 15 | — | 2.5 | No Tack |
| 16 | — | 2 | |
| 17 | — | 3 | Tacky |
| 18 | 10 parts A | 4 | No tack |
| 19 | 30 parts A | 4 | No tack - release of A |
| 20 | 10 parts B | 2.5 | No tack |
| 21 | 30 parts B | 2.5 | Slight tack - good surface |
| 22 | 10 parts C | 3 | |
| 23 | 30 parts C | 2.5 | Slight tack - poor cohesion |
| 24 | 10 parts D | 2.5 | No tack after 10 minutes |
| 25 | 10 parts E | — | No tack after 10 minutes |
| 26 | 10 parts F | 8 | No tack |
| 27 | 10 parts G | 4 | No tack |
| 28 | — | 4 | Tacky |
| 29 | — | 5.5 | Very tacky |
| 30 | — | 11 | V. tacky - low consistency |

A = propylene glycol
B = glycerol
C = D-sorbitol
D = polyethylene glycol 200
E = polyethylene glycol 600
F = polyethylene glycol 1000, melted
G = polyethylene glycol 1000, 1 g/ml in water From these results, it is apparent that the rate of cure of the silicone composition can be adjusted by variation of the catalyst and inhibitor proportions employed and by variation of the ratio of Parts A and B, which varies also the ratio of the polysiloxanes. The cure rate is also influenced by the nature and proportion of the hydrophilic material used. Nevertheless it will be apparent that one may provide a formulation capable of curing within 10 minutes or less, which is appropriate to permit mixing of the formulation and application to the body where it cures within a few minutes. For many dressing applications, the formulations which cure to a non-tacky condition are preferred, but those which cure to a tacky condition are also acceptable for some applications.

EXAMPLE 2

Formulations were prepared by mixing ingredients in the proportions shown in Table 2. Discs were prepared by mixing the components of each formulation using a Heidolph RGL 500 bench homogenizer. The mixed formulations were pressed into a mould between two 50 micron polyester films then cured at 22° C. to give a matrix with a thickness 2 to 2.2 mm and 2 cm discs were punched therefrom. To determine swelling, each disc was weighed then placed into 200 ml of deionized water (pH=6) at 22° C. Each disc was removed and all water removed from its surface using a filter paper, then weighed again. The Weight Swelling Ratio $W_s/W_d$ is recorded as the ratio between weight in the swollen ($W_s$) and dry ($W_d$) state.

TABLE 2

| Component | Formulation | | | | |
|---|---|---|---|---|---|
| | 1 | 2 | 3 | 4 | 5 |
| Silicone Part 1A | 50 | 50 | 50 | 30 | 50 |
| Silicone Part 1B | — | — | — | 10 | — |
| Silicone Part 2B | 10 | 10 | 10 | — | 10 |
| Propylene glycol | 15 | — | — | — | — |
| Polyethylene glycol 200 | — | — | 15 | — | — |
| Glycerol | — | — | — | 15 | 15 |
| Sorbitol | — | 15 | — | — | — |
| Cellulosic material 1 | 25 | 25 | 25 | 25 | 25 |
| Sodium acetate | — | — | — | 20 | — |
| Cure time at 22° C. | 20' | 3' | >2 H | >1 H | 8' |

The time required for cure of these compositions is dependent upon the polyol used and presence or absence of sodium acetate as well as on the nature of the Silicone Part B.

Formulation 3, which included polyethylene glycol, and Formulation 4, which included sodium acetate and an inhibited catalyst, failed to cure within 10 minutes of mixing. The Formulations containing the Silicone Part 2B became cured in 20 minutes or less, with those containing sorbitol or glycerol curing more quickly than the others. It was found that the discs swelled in water and the discs of formulation 4 swelled most quickly to double their size within 1 to 3 hours and continued to swell at a substantially constant rate throughout a 24 hour period. Formulations 2 and 5 swelled in a substantially constant fashion over 24 hours to a Weight Swelling Ratio in the range 1.6 to 5, with Formulation 5 showing the most constant swelling and the degree of swelling of Formulation 5 being greater than that of Formulation 2. Formulations 1 and 3 swelled at the same rate as each other for 8 hours and then showed a slower swelling.

EXAMPLE 3

The swelling and bioadhesive properties were examined of discs made from formulations comprising 60 parts of a mixture of silicone Parts 1A and 1B in a ratio of 8:3, 25 parts of cellulosic materials 1 to 7 and 15 parts of glycerol. The discs were made as described in Example 2 except that the curing was conducted at 100° C. The discs were allowed to swell in deionized water (pH=6) at 22° C. for 48 hours and tested as described in Example 2. Results are shown in Table 3.

TABLE 3

| Cellulosic Material | $W_s/W_d$ | W % | Remarks |
|---|---|---|---|
| 1 | 6.3 | 530 | Slight tack, gel like surface |
| 2 | 6.4 | 540 | Dry surface |
| 3 | 3.5 | 250 | Dry surface |
| 4 | 4.6 | 360 | Dry surface |
| 5 | 6.6 | 560 | Very dry surface |
| 6 | 2.3 | 130 | Very dry surface |
| 7 | 1.9 | 90 | Very dry surface |

As can be seen from Table 3 the Formulation comprising cellulosic material 1 demonstrated surface tackiness whereas the others did not. Maximum swelling was demonstrated by the discs of Formulations comprising cellulosic materials 1, 2 or 5. Discs formed from the Formulation including cellulosic material 1 also demonstrated adherence to a mucous membrane as in the buccal cavity. W % is the weight increase due to swelling.

EXAMPLE 4

The swelling behaviour of discs made, as described in Example 3, from formulations comprising materials in the proportions shown in Table 4 was studied.

TABLE 4

| Component | Formulation | | | | | |
|---|---|---|---|---|---|---|
| | 1 | 2 | 3 | 4 | 5 | 6 |
| Silicone Part 1A | 62.5 | 50 | 45.85 | 41.7 | 37.5 | 33.3 |
| Silicone Part 1B | 12.5 | 10 | 9.15 | 8.3 | 7.5 | 6.7 |
| Glycerol | 0 | 15 | 20 | 25 | 30 | 35 |
| Cellulosic material 1 | 25 | 25 | 25 | 25 | 25 | 25 |

A formulation containing 40% glycerol needed 15 minutes at 100° C. to be fully cured. The sample discs were allowed to swell for 48 hours in deionized water (pH=6) at 20° C. The results are given in Table 5.

TABLE 5

| Formulation | Ws/Wd | Remarks |
|---|---|---|
| 1 | 1.7 | Very dry surface |
| 2 | 6.3 | Slight tack, gel like surface |
| 3 | 7.2 | Tacky, gluey surface |
| 4 | 8.3 | Tacky, gluey surface |
| 5 | 2.3 | Very gluey surface |
| 6 | 1.1 | Decrease in volume |

As can be seen, presence of glycerol together with the cellulosic material in the Formulation provides a dramatic increase in swelling and bioadhesion. These results also show that the proportion of glycerol employed can be optimized in order to get desired swelling and good bioadhesion. Maximum swelling was obtained using 25% glycerol. At glycerol levels of 35 and 40% a decrease in volume of the disc is observed due to loss of integrity of the matrix after maximum swelling. The swelling and bioadhesion behaviour was examined of samples made from formulations using proportions of material as shown in Table 6. Discs were prepared and swelled for 48 hours in deionized water (pH=6) at 20° C. The results are reported in Table 7.

TABLE 6

| Component | Formulation | | | |
|---|---|---|---|---|
| | 7 | 8 | 9 | 10 |
| Silicone Part 1A | 70.8 | 62.5 | 50.0 | 29.4 |
| Silicone Part 1B | 14.2 | 12.5 | 10 | 5.8 |
| Glycerol | 15 | 15 | 15 | 15 |
| Cellulosic material 1 | 0 | 10 | 25 | 50 |

TABLE 7

| Formulation | Ws/Wd | W % | Remarks |
|---|---|---|---|
| 7 | 1.8 | 80 | Very dry surface |
| 8 | 2.1 | 110 | Very slight tack |
| 9 | 6.3 | 530 | Slight tack |
| 10 | 5.3 | 430 | Gel like surface |

The results show that for a constant glycerol content a minimum proportion of cellulosic material is necessary in order to get significant swelling and tack. At 50% cellulosic polymer (which represents only 35% silicone in the composition) cohesion of the swelled material is poor, which results in an erosion of the surface of the disc and loss of the cellulosic material into the solution.

The swelling behaviour of sample discs made as described in Example 3 using 50 parts of Silicone Part 1A, 10 parts of Silicone Part 1B, 15 parts glycerol and 25 parts cellulosic material 1 was examined. Sample discs were allowed to swell over 48 hours at 20° C. at eight different pH: pH=1.2, 2, 3, 4, 5, 6, 7 and 8. The Weight Swelling Ratio, Ws/Wd, was recorded every hour (H) during the first eight hours and then after 24 hours, 48 hours and every day up to 6 days. The results are reported in Table 8.

TABLE 8

| (H) | pH 1.2 | pH 2 | pH 3 | pH 4 | pH 5 | pH 6 | pH 7 | pH 8 |
|---|---|---|---|---|---|---|---|---|
| 0 | 1.000 | 1.000 | 1.000 | 1.000 | 1.000 | 1.000 | 1.000 | 1.000 |
| 1 | 1.101 | 1.134 | 1.208 | 1.277 | 1.290 | 1.310 | 1.297 | 1.286 |
| 2 | 1.135 | 1.184 | 1.293 | 1.438 | 1.462 | 1.466 | 1.466 | 1.434 |
| 3 | 1.173 | 1.229 | 1.389 | 1.619 | 1.643 | 1.652 | 1.648 | 1.601 |
| 4 | 1.204 | 1.274 | 1.468 | 1.787 | 1.827 | 1.816 | 1.817 | 1.738 |
| 5 | 1.235 | 1.310 | 1.540 | 1.959 | 2.011 | 2.002 | 1.988 | 1.899 |
| 6 | 1.264 | 1.349 | 1.605 | 2.127 | 2.176 | 2.178 | 2.149 | 2.049 |
| 7 | 1.291 | 1.385 | 1.677 | 2.293 | 2.346 | 2.344 | 2.311 | 2.205 |
| 8 | 1.314 | 1.416 | 1.742 | 2.437 | 2.489 | 2.500 | 2.444 | 2.346 |
| 24 | 1.607 | 1.852 | 2.548 | 3.656 | 3.682 | 3.813 | 2.644 | 3.610 |
| 32 | 1.704 | 2.019 | 2.772 | 4.123 | 4.114 | 4.218 | 4.033 | 4.020 |
| 48 | 1.821 | 2.243 | 3.101 | 4.663 | 4.668 | 4.920 | 4.570 | 4.579 |
| 72 | 1.995 | 2.536 | 3.448 | 5.07 | 5.04· | 5.266 | 4.918 | 4.921 |
| 144 | 2.19 | 3.198 | 3.933 | 5.228 | 5.076 | 5.262 | 4.976 | 4.961 |

For all pH values swelling is linear until the 8th hour. At any time, maximum swelling was obtained for pH between 4 and 7 (Ws/Wd=2.4 to 2.5 after 8 hours) much superior than at very acidic pH (Ws/Wd=1.3 at pH=1.2 after 8 hours).

EXAMPLE 5

An illustrative Formulation was prepared comprising 37.5 parts of silicone Part 2A and 25 parts of silicone Part 2B, 9 parts of sorbitol, 19.5 parts of glycerol and 9 parts of the drug tetracycline hydrochloride. Matrices were formed from this composition by casting the Formulation into a cavity mould and allowing the Formulation to cure at room temperature. The matrices weighed 961.3 mg, had an average diameter of 1.275 cm, an average thickness of 0.66 cm and a surface area of about 5.2 $cm^2$. Release of the drug from the cured Formulation was examined by a dissolution study at pH 4.5 according to the USP XXXI Standard test and the basket method using a fully automatic SOTAX AT6, including the dissolution apparatus itself, linked to a microprocessor-controlled pneumatic pump and fraction collector. Six dissolution vessels were filled with 900 ml of dissolution medium. One matrix was placed in each basket. Stirring was effected at 150 rpm with the outer thermostatic bath at 37°±0.1° C. 5 ml samples of dissolution medium were collected at preprogrammed time intervals with automatic replenishment with fresh medium. UV spectra of these samples were recorded with a UVIKON 860 spectrophotometer and tetracycline hydrochloride released was calculated from the calibration curve. The mean value of the cumulative amount, as a percentage, of tetracycline hydrochloride released from the six cells is shown in Table 9.

TABLE 9

| Time (Hrs) | Mean Value (%) |
|---|---|
| 0 | 0 |
| 0.5 | 1.30 |
| 1 | 1.70 |
| 2 | 2.36 |
| 3 | 2.85 |
| 4 | 3.24 |
| 5 | 3.56 |
| 6 | 3.97 |
| 12 | 5.80 |
| 18 | 7.68 |
| 24 | 9.62 |
| 36 | 14.84 |
| 48 | 18.57 |
| 60 | 22.98 |
| 72 | 27.01 |
| 84 | 30.52 |
| 96 | 34.46 |
| 108 | 38.57 |
| 120 | 41.95 |
| 132 | 46.02 |
| 144 | 48.88 |
| 156 | 52.38 |
| 168 | 55.33 |
| 180 | 58.51 |
| 192 | 60.44 |
| 204 | 67.59 |
| 216 | 68.64 |
| 228 | 69.56 |
| 240 | 70.20 |

As can be seen 70% of the tetracycline hydrochloride was released progressively over the 10 day period. These results show that about 0.317% tetracycline hydrochloride was released per hour and 7.6% was released per day during dissolution. The release occurred at substantially constant rate over the whole test period. The proportion liberated attained a plateau after 8.5 days and 70.2% of the drug had been released at the ninth day. At the end of the dissolution test the mean surface area of the matrices was 8.7 cm i.e. 1.7 times the original surface area.

The experiment was repeated using second, third and fourth illustrative Formulations; these Formulations comprised respectively 41.7 parts of silicone Part 2A and 27.8 parts of silicone Part 2B, 21.5 parts of glycerol and 9 parts of tetracycline hydrochloride; 35.7 parts of silicone Part 2A, 23.8 parts of silicone Part 2B, 21.5 parts of glycerol, 10 parts of sorbitol and 9 parts of tetracycline hydrochloride; and 29.7 parts of silicone Part 2A, 19.8 parts of silicone Part 2B, 21.5 parts of glycerol, 20 parts of sorbitol and 9 parts of tetracycline hydrochloride. When the second illustrative Formulation was subjected to the dissolution test it was found that 25% of the drug was released in the first 100 hours and a further 25% of the drug was released in the next 92 hours; the release during each period was at substantially constant rate. When the third illustrative Formulation was subjected to the dissolution test it was found that 60% of the drug was released during the first 120 hours and a further 10% was released during the subsequent 72 hours, the release during each period being at a substantially constant rate. When the fourth illustrative Formulation was subjected to the dissolution test it was found that 50% of the drug was released during the first 40 hours, a further 25% was released in the next 70 hours and a further 8% was released during the subsequent 40 hours but no further release of the drug occurred after 150 hours, the release during each period being at a substantially constant rate. Thus, high release rates are dependent on presence of sorbitol as well as glycerol, the fastest release being obtained by use of the largest proportion of sorbitol.

That which is claimed is:

1. A sustained release formulation suitable for use as a dressing in or on the human or animal body comprising 10–70 parts by weight of a therapeutic or diagnostic agent (A) dispersed in 90–30 parts by weight of a vehicle (B) therefor which vehicle includes
   (1) from 5 to 40 weight % of a hydrophilic component selected from the group consisting of polyethylene glycols, propylene glycols, glycerol, sorbitol, mannitol and lactose;
   (2) a curable silicone composition which is formulated to cure at room temperature within 10 minutes of mixing and application to the body, the curable composition consisting of a polysiloxane having alkylhydrogen siloxane units, a polysiloxane having unsaturated groups for reaction therewith and a platinum or rhodium catalyst for the hydrosilylation reaction; and
   (3) a modulating component which is different from the hydrophilic component (1) and serves to modulate release of the therapeutic or diagnostic agent (A) from a dressing formed from the formulation when the dressing is in use, the modulating component being provided by 10–40 weight % of an organic substance having two or more hydroxyl groups per molecule or 10–45 weight % of a hydrophilic polymer which swells in an aqueous medium.

2. A formulation according to claim 1 wherein the hydrophilic component (1) comprises glycerol and provides 10% to 30% by weight of the vehicle.

3. A formulation according to claim 1 wherein the organic substance (I) is selected from the group consisting of the solid polyethylene glycols of molecular weight greater than 600, sorbitol, mannitol and lactose.

4. A formulation according to claim 1 wherein the hydrophilic polymer (II) is selected from the group consisting of hydroxypropylcellulose, carboxymethylcellulose and sodium carboxymethylcellulose.

5. A formulation according to claim 1 wherein the polysiloxanes provide from 20% to 80% by weight of the vehicle.

6. A formulation according to claim 1 which also comprises another organic material imparting bioadhesive properties to the cured formulation.

7. A formulation according to claim 1 wherein the agent (A) is selected from the group consisting of antiseptic, antiinflammatory, cardiovascular, antacid, bronchodilator, analgesic, alpha-1 blocker, acetylcholine esterase inhibitor, diuretic, antiaggregant, sedative, anticonvulsant agents, vitamins, agents for treating gastric and duodenal ulcers, and proteolytic enzymes.

8. A method of delivering a therapeutically or diagnostically active agent to the human or animal body comprising the steps of:
   (a) providing a formulation according to claim 1 which is capable of forming a dressing in or on the body;
   (b) casting the formulation on the body or in an artificial or natural cavity thereof; and
   (c) curing the formulation at the site of application, forming a dressing for sustained release of the therapeutic or diagnostic agent (A) from the dressing to the body.

9. A formulation according to claim 1 for administration to a cavity of the body comprising from 10 to 70 parts by weight of the agent (A) and from 90 to 30 parts by weight of the vehicle (B), the vehicle (B) comprising 10 to 40 parts by weight of the hydrophilic component (a), 40 to 80 parts by weight of the polysiloxanes and 10 to 40 parts by weight of a hydrophilic material (I) selected from the group consisting of polyethylene glycols of molecular weight greater than 600, sorbitol, mannitol and lactose.

10. A method of treatment of the human or animal body to provide a dressing thereon from which a therapeutic or diagnostic agent (A) is released to the body comprising the steps of:

(a) providing a sustained release formulation according to claim 1;

(a) applying the formulation to intact or damaged skin of the body, or to a natural or artificial cavity of the body, and allowing the formulation to cure on the site of application thereof.

11. A formulation according to claim 1 wherein the organic substance (I) comprises sorbitol and provides from 5% to 25% by weight of the vehicle.

12. A formulation according to claim 1 wherein the hydrophilic polymer comprises sodium carboxymethylcellulose and provides from 10% to 45% by weight of the vehicle.

* * * * *